United States Patent [19]

Friedman et al.

[11] Patent Number: 4,925,029

[45] Date of Patent: May 15, 1990

[54] COMBINATION MAILER

[75] Inventors: Dale Friedman, East Brunswick; Louis P. Mennella, Princeton Junction, both of N.J.

[73] Assignee: Innovative Sampling Technologies Inc., New York, N.Y.

[21] Appl. No.: 325,236

[22] Filed: Mar. 17, 1989

[51] Int. Cl.⁵ .................. B65D 73/00; B65D 81/02
[52] U.S. Cl. .................... 206/473; 206/581; 206/459; 206/620; 206/588; 206/591; 206/594
[58] Field of Search ............... 206/581, 472, 473, 474, 206/521, 588, 591, 594

[56] References Cited

U.S. PATENT DOCUMENTS

| 4,221,221 | 9/1980 | Ehrlich | 206/581 |
| 4,569,082 | 2/1986 | Ainsworth et al. | 206/581 X |
| 4,720,012 | 1/1988 | Dufour | 206/472 |
| 4,758,229 | 7/1988 | Doerschner | 206/63.3 |

FOREIGN PATENT DOCUMENTS

| 584700 | 10/1959 | Canada | 206/474 |
| 730998 | 3/1966 | Canada | 206/474 |

Primary Examiner—William Price
Attorney, Agent, or Firm—Lerner, David, Littenberg, Krumholz & Mentlik

[57] ABSTRACT

A combination mailer has a jacket which includes opposable leaves which are separable from a more rigid web. Each of the leaves has a cavity formed therein for containing a product sample. A vial or ampule containing another product sample is positioned between the opposable leaves and removably connected to the spine. Optionally, the jacket includes a closure device for maintaining the opposable leaves in a closed position around the vial or ampule.

22 Claims, 2 Drawing Sheets

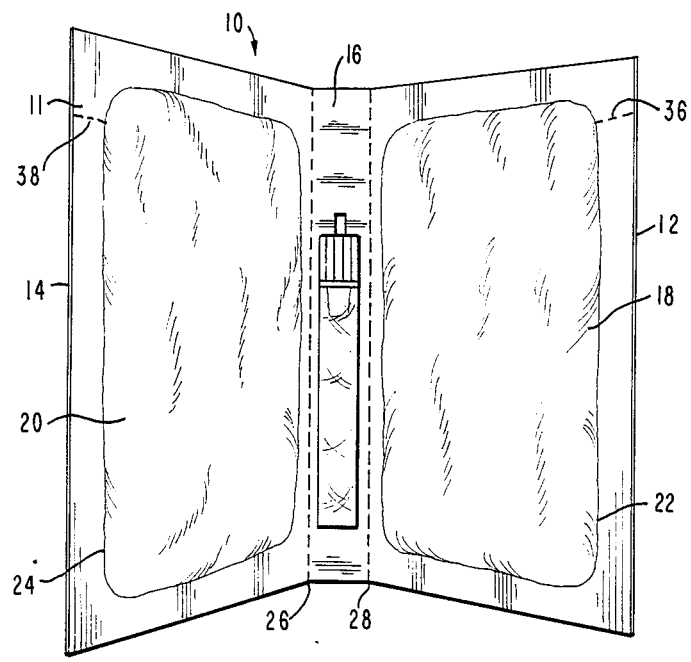
FIG. 1
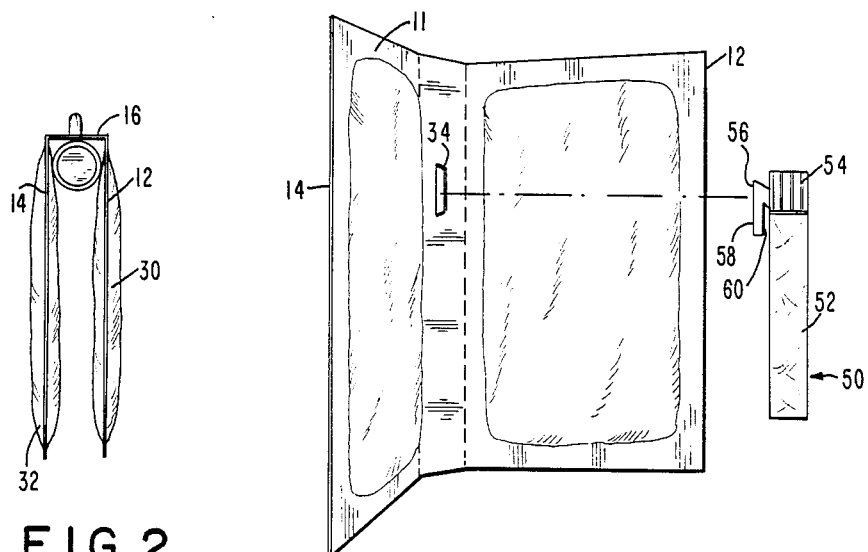
FIG. 2
FIG. 3

COMBINATION MAILER

BACKGROUND OF THE INVENTION

In order to promote and advertise their products, companies in the cosmetic, fragrance and toiletry industries frequently prepare samples of their products for distribution to the public.

In the cosmetic and toiletry industries, these samples are often in the form of packets or pouches which are filled with a small portion of the product, which is in many cases a fluent or flowable material, and these packets are then distributed either at the sales counters of retail outlets or as an enclosure in mailings to particular segments of the general public. In the fragrance industry, samples of fragrances have in the past been packaged in small glass or plastic vials attached to a thin cardboard jacket. These samples are also distributed at the sales counters of retail outlets, but are difficult to distribute in mailings because of the fragile nature of the glass or plastic vials.

Additionally, cosmetic lines often include a multitude of items which come in liquid, solid and cream or lotion form. In order to provide samples of more than one product, distributors presently have to prepare individual samples and hand them out at sales counters separately, even where they desire particular product samples to be associated with one another. Therefore, distributors cannot be assured that the samples which they intend to be distributed together are actually being so distributed.

Thus, there exists the need for a package by which samples of more than one product can be distributed in association with one another. Also, there exists the need for a package in which vials containing a sample of a product can be reliably distributed through the mail without being broken by mechanical shock and handling. In particular, there is a need for packages which can distribute samples in these manners at low cost.

SUMMARY OF THE INVENTION

In accordance with the present invention, these needs have now been addressed by the invention of a combination mailer package including a jacket having a pair of opposable leaves, at least one of the leaves having means for retaining a first fluent material, and means for retaining a product between the leaves so as to be protected from mechanical shock thereby. The leaves may include a first sheet and a second sheet sealed along spaced sealing lines to form a storage cavity for retaining the first fluent material.

In accordance with one embodiment of the invention, the jacket further includes means for releasably connecting the leaves to one another so that the leaves may be separated from the jacket without creating an opening for dispensing the fluent material.

Additionally, the means for retaining a product may include means for retaining a second fluent material between the leaves. Preferably, the means for retaining a second fluent material includes a vial and a closure for the vial. Further, the closure for the vial may include hook means for detachably connecting the vial to the jacket between the opposable leaves.

In another embodiment, the jacket may include a connecting web connectable along a first edge to one of the opposable leaves and connectable along a second edge to another of the opposable leaves. Preferably, the means for retaining a second fluent material includes a vial and a closure for the vial, wherein the closure for the vial has hook means for detachably connecting the vial to the connecting web.

In yet another embodiment, the jacket may include slit means on one of the opposable leaves and tab means on another of the opposable leaves sized for operative engagement with the slit means to keep the opposable leaves in a closed position.

Desirably, the means for retaining the second fluent material has a transverse cross-section which is less than the width of the connecting web and a length which is less than the length of the jacket.

Additionally, the leaves containing fluent material may include indication means for providing a location for opening the storage cavity to dispense the fluent material.

Preferred embodiments of the present invention provide combination mailer packages which are of simple construction and inexpensive to manufacture.

Moreover, the preferred packages according to the present invention provide a reliable way to distribute samples of more than one product in association with one another.

Additionally, the preferred packages according to the present invention enable the reliable distribution without breakage of vials or ampules via mailings to the public.

These and other objects will become apparent, as will a better understanding of the structure and operation of the present invention, when reference is made to the description which follows taken with the drawings in which:

BRIEF DESCRIPTION OF THE DRAWINGS

FIG. 1 is a perspective view of the combination mailer package in accordance with the present invention, FIG. 2 is a cross-sectional view taken along line 2—2 of FIG. 1, FIG. 3 is an exploded view showing the assembly of the elements of the combination mailer package of FIG. 1.

DETAILED DESCRIPTION

Figure 4:
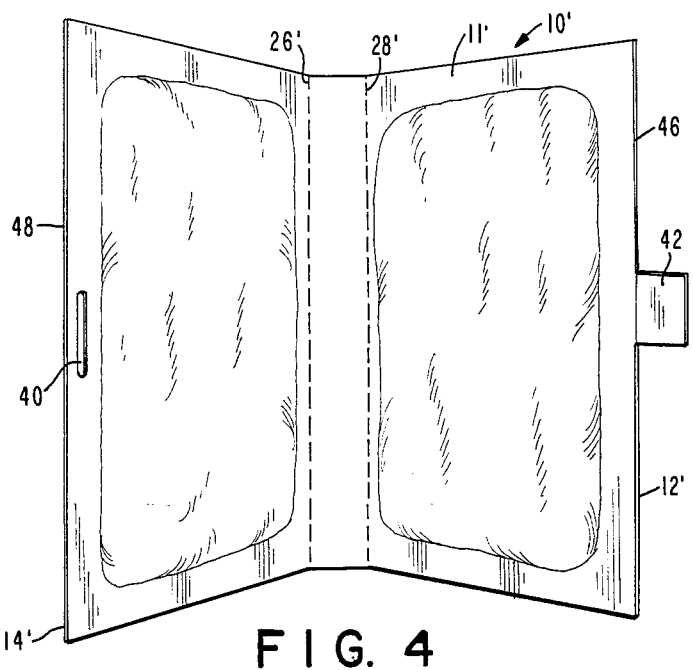
FIG. 4 is a perspective view of an alternate embodiment of the jacket of the combination mailer package in accordance with the present invention.

Referring to FIG. 1, there is illustrated a preferred embodiment of the combination mailer package 10 in accordance with the present invention. Package 10 includes a jacket 11 which has opposable leaves 12 and 14 connected to a web 16 in a manner which will be discussed further hereinbelow. Leaves 12 and 14 are typically formed from two sheets of material sealed together along sealing lines 22 and 24, but not sealed together at interior portions 18 and 20, thereby defining cavities 30 and 32 therein.

Web 16 preferably is also formed from two sheets of the same material as used to form leaves 12 and 14, but generally has a smaller surface area. In forming web 16, however, the sheets of material are desirably sealed together over their entire surface, so that web 16 is stronger and more rigid than leaves 12 and 14 and acts as a spine to support the overall package structure.

The sheets used to fabricate leaves 12 and 14 and web 16 may be formed from and impervious material capable of retaining a fluent material therebetween. Preferably, however, the sheets are formed from a laminate consisting of layers of plastic, paper and metal foil. Most preferably, the sheets are formed from a laminate consisting of two inner plastic layers followed by a layer of a metal foil, a paper layer and an outer plastic layer. Both the innermost plastic layer and the outer plastic layer may have printed thereon the product names, logos, ingredients, instructions, or any other information desired.

Leaves 12 and 14 are connected to web 16 along connecting lines 26 and 28. Typically, connecting lines 26 and 28 are formed with perforations or in a similar manner which allows leaves 12 and 14 to be easily separated from web 16.

Additionally, leaves 12 and 14 are connected to web 16 in a manner which causes the leaves to normally oppose one another in book-like fashion. Thus, as leaves 12 and 14 are rotated away from one another a rotational stress is developed along connecting lines 26 and 28 and a flexural stress is developed in web 16. As the leaves are released, they move towards one another as these stresses are relieved.

As can be seen in FIG. 3, web 16 includes slot 34 for connecting vial or ampule 50 to jacket 11. Ampule 50 is substantially similar to the ampules or vials typically used in the fragrance industry. A cylindrical glass or plastic container 52 is usually closed by a plastic cap 54. A hook portion 56 is formed integrally with the cap 54 and is sized to insert into slot 34 on web 16. Once hook 56 has been inserted into slot 34, ampule 50 is slid downward so that web 16 is pushed into the connecting space 60 formed between container 52 and the depending leg 58 of hook 56, and the ampule 50 is firmly held in place.

Preferably, ampule 50 is sized and shaped to fit entirely within jacket 11 in a manner which enables leaves 12 and 14 to close to the position shown in FIG. 2. Thus, the cross-section of container 52 and cap 54 are typically smaller than the width of web 16 between connecting lines 26 and 28. Also, the length of ampule 50 is desirably less than the length of web 16 and leaves 12 and 14 so that ampule 50 does not protrude from jacket 11. In this regard, slot 34 may be positioned on web 16 to adjust the position of ampule 50 within jacket 11. Thus, for short ampules slot 34 may be located towards the center of web 16, and for longer ampules slot 34 may be located closer to one end of web 16.

Although reference has been made to an ampule having a cylindrical cross-section, a container of any cross-sectional shape may be employed. Further, other products such as brushes, eyeliner pencils, jewelry, or other desired items may be connected between leaves 12 and 14.

In order to distribute samples of more than one product using the package 10 of the present invention, product samples are filled into cavities 30 and 32 which are then sealed closed along sealing lines 22 and 24, respectively. These samples typically consist of creams or lotions, but may include powders, liquids, pastes, solids or any other materials which may be retained by the sheet material forming cavities 30 and 32. Further, the sample in cavity 32 may be of a different product or of a different physical form than the sample contained in cavity 30 or, if desired, only one of the cavities need be filled with a product sample. Once cavities 30 and 32 have been sealed closed, access to the product samples may be had by tearing at tear lines 36 or 38 formed in the sealed portions of leaves 12 and 14. Alternatively, tear lines 36 and 38 may be replaced by notches, holes or other tear indications, or access to cavities 30 and 32 may be gained by cutting open cavities 30 and 32 with a scissors or other sharp instrument.

Ampule 50 is filled with yet another sample which may be the same as or different than the samples contained in cavities 30 and 32. Thus, ampule 50 may contain a solid, powder, lotion or a liquid. Once filled, ampule 50 is attached to jacket 11 so that the samples can be distributed in combination with one another.

Figure 5:
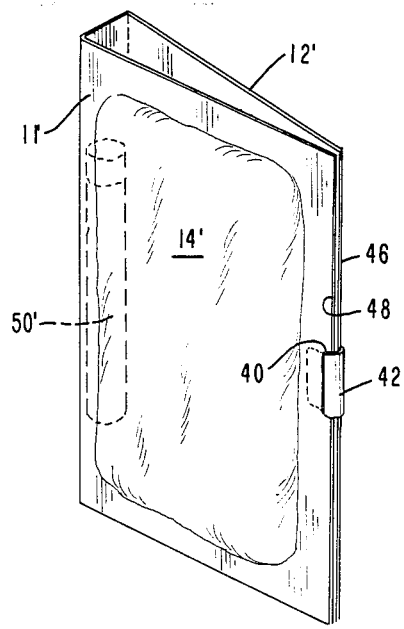
FIG. 5 is a perspective view showing the jacket of the combination mailer package of FIG. 4 in a closed position with the ampule therewithin.

In an alternate embodiment, combination mailer package 10' is the same as combination mailer package 10 described above but jacket 11' includes a closure device for maintaining opposable leaves 12' and 14' in a closed position, as shown in FIGS. 4 and 5. Thus, leave 12' includes tab 42 along outer edge 46 opposite connecting line 28', and leave 14' includes slit 40 adjacent outer edge 48 opposite connecting line 26', at a location opposite tab 42. Tab 42 is sized and shaped to fit into slit 40 when jacket 11' is in a closed position around ampule 50' with outer edges 46 and 48 adjacent one another, and thereby maintains this closed position. Other closure devices may alternatively be used, such as snaps, clips, velcro strips or the like.

While the foregoing description presents the preferred embodiments of the device and assembly in accordance with the present invention, it will be appreciated that certain changes and modifications may be made in the structure of these disclosed arrangements without departing from the spirit and scope of the invention as set forth in the appended claims.

We claim:

1. A package comprising
   a jacket having a pair of opposable leaves, at least one of said leaves having a first sheet and a second sheet sealed along spaced sealing lines to form a storage cavity therebetween for retaining a first fluent material, and
   means for retaining a product between said leaves so as to be protected from mechanical shock by said first fluent material stored within said at least one of said leaves.

2. A package as claimed in claim 1 wherein said jacket includes means for releasably connecting said leaves to one another so that said leaves may be separated from said jacket without creating an opening for dispensing said fluent material.

3. A package as claimed in claim 1 wherein said means for retaining a product includes means for retaining a second fluent material between said leaves.

4. A package as claimed in claim 3 wherein said means for retaining a second fluent material includes a vial and a closure for said vial.

5. A package as claimed in claim 4 wherein said for said vial includes hook means for detachably connecting said vial to said jacket between said opposable leaves.

6. A package as claimed in claim 1 wherein said jacket includes a connecting web connectable along a first edge to one of said opposable leaves and connectable along a second edge to said other of said opposable leaves.

7. A package as claimed in claim 6 wherein said connecting web is more rigid than said opposable leaves.

8. A package as claimed in claim 7 wherein said means for retaining a product includes means for retaining a second fluent material between said leaves.

9. A package as claimed in claim 8 wherein said means for retaining said second fluent material includes, a vial and a closure for said vial.

10. A package as claimed in claim 9 wherein said closure for said vial includes hook means for detachably connecting said vial to said connecting web.

11. A package as claimed in claim 8 wherein said means for retaining said second fluent material has a transverse cross-section which is less than the width of said connecting web between said first edge and said second edge.

12. A package as claimed in claim 8 wherein said means for retaining said second fluent material has a length which is less than the length of said jacket.

13. A package as claimed in claim 1 wherein said first and second sheets are formed from a laminated material.

14. A package as claimed in claim 13 wherein said laminated material comprises a plastic inner layer, a metallic foil first intermediate layer, a paper second intermediate layer, and a plastic outer layer.

15. A package as claimed in claim 1 wherein said at least one of said leaves includes indication means for providing a location for opening said storage cavity in order to dispense said first fluent material.

16. A package as claimed in claim 1 further including closure means to keep said opposable leaves in a closed position.

17. A package as claimed in claim 16 wherein said closure means comprises slit means on one of said opposable leaves and tab means on said other of said opposable leaves sized for operative engagement with said slit means.

18. A package comprising
a jacket having a pair of opposable leaves, at least one of said leaves having means for retaining a first fluent material, and
a vial and a closure for said vial to retain a second fluent material between said leaves so as to be protected from mechanical shock by said first fluent material associated with said at least one of said leaves.

19. A package as claimed in claim 18, wherein said closure for said vial includes hook means for detachably connecting said vial to said jacket between said opposable leaves.

20. A package comprising
a jacket having a pair of opposable leaves, at least one of said leaves having means for retaining a first fluent material, said jacket including a connecting web connectable along a first edge to one of said opposable leaves and connectable along a second edge to said other of said opposable leaves, said connecting web being more rigid than said opposable leaves, and
a vial and a closure for said vial for retaining a second fluent material between said leaves so as to be protected from mechanical shock by said first fluent material associated with said at least one of said leaves.

21. A package as claimed in claim 20 wherein said closure for said vial includes hook means for detachably connecting said vial to said connecting web.

22. A package comprising
a jacket having a pair of opposable leaves, at least one of said leaves having means for retaining a first fluent material, said jacket including a connecting web connectable along a first edge to one of said opposable leaves and connectable along a second edge to said other of said opposable leaves, said connecting web being more rigid than said opposable leaves, and
means for retaining a second fluent material between aid leaves so as to be protected from mechanical shock by said first fluent material associated with said at least one of said leaves, said means for retaining said second fluent material having a transverse cross-section which is less than the width of said connecting web between said first edge and said second edge.

* * * * *